United States Patent [19]

Shirai et al.

[11] 4,002,666

[45] Jan. 11, 1977

[54] PROCESS FOR THE PREPARATION OF OPTICALLY ACTIVE p-HYDROXYPHENYLGLYCINE

[75] Inventors: Tadashi Shirai, Musashino; Yasuhisa Tashiro, Yokohama; Shigeru Aoki, Tokyo, all of Japan

[73] Assignee: Nippon Kayaku Kabushiki Kaisha, Tokyo, Japan

[22] Filed: Oct. 22, 1974

[21] Appl. No.: 516,963

[30] Foreign Application Priority Data

Oct. 23, 1973 Japan .............................. 48-118542

[52] U.S. Cl. .............................. 260/471 C; 260/463; 260/477; 260/479 R; 260/501.11; 260/519
[51] Int. Cl.$^2$ ................ C07C 19/00; C07C 103/46; C07C 103/84; C07C 125/06
[58] Field of Search ...... 260/471 C, 479 R, 501.11, 260/519

[56] References Cited
UNITED STATES PATENTS

| | | | |
|---|---|---|---|
| 3,651,138 | 3/1972 | Yee et al. ................ | 260/501.11 X |
| 3,796,748 | 3/1974 | Holdrege .................... | 260/501.11 |
| 3,803,213 | 4/1974 | Weber et al. .................. | 260/479 R |
| 3,832,388 | 8/1974 | Lorenz .......................... | 260/519 X |
| 3,869,505 | 3/1975 | Palmer .......................... | 260/479 R |

OTHER PUBLICATIONS

Greenstein, et al., Chemistry of the Amino Acids, vol. 1, (1961), pp. 718–721.

Primary Examiner—Richard L. Raymond
Attorney, Agent, or Firm—Russell & Nields

[57] ABSTRACT

Optically active p-hydroxyphenylglycine is prepared by reacting a racemic compound of a specified p-hydroxyphenylglycine derivative with optically active α-phenylethylamine to form a corresponding salt, obtaining two types of optically active salts therefrom by fractional crystallization, and obtaining optically active p-hydroxyphenylglycine by decomposition and hydrolysis of at least one of the optically active salts.

10 Claims, No Drawings

PROCESS FOR THE PREPARATION OF OPTICALLY ACTIVE P-HYDROXYPHENYLGLYCINE

DETAILED DESCRIPTION OF THE INVENTION

This invention relates to a process for the preparation of optically active p-hydroxyphenylglycine.

There have been heretofore proposed and known methods for the resolution of p-hydroxyphenylglycine, including a method using dehydroabietylamine (German Preliminary Patent Publication No. 2,147,620) and a method for resolving benzyloxycarbonyl derivatives of p-hydroxyphenylglycine by means of quinine (J. Chem. Soc. (C) 1971, 1920, London: The Chemical Society).

However, such methods have disadvantages that, in the former, dehydroabietylamine used as a resolving agent generally contains impurities in an amount as large as 50% of it and accordingly it must be purified sufficiently in practical application, while, in the latter, the use of expensive quinine is unsuitable for the production of p-hydroxyphenylglycine on an industrial scale.

We have conducted an extensive study of a novel method for the preparation of optically active p-hydroxyphenylglycine, and found that optically active p-hydroxyphenylglycine can be produced with extreme ease by reacting a racemic compound of a p-hydroxyphenylglycine derivative represented by the following general formula

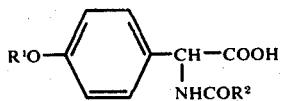

(wherein $R^1$ represents a hydrogen atom, a lower alkyl group or an acyl group, and $R^2$ represents a hydrogen atom, a lower alkyl group, a phenyl group or a benzyloxy group) with optically active α-phenylethylamine to form a corresponding salt, subjecting the salt to fractional crystallization for optical resolution to obtain two kinds of optically active salts, decomposing the two kinds of optically active salts by means of an acid or an alkali to obtain the respective optically active p-hydroxyphenylglycine derivatives, and hydrolyzing the two optically active derivatives with an acid selected from the group consisting of hydrochloric acid, sulfuric acid, hydrobromic acid and hydroiodic acid to obtain optically active p-hydroxyphenylglycine. The present invention is based upon the above finding.

In the general formula mentioned above, the lower alkyl group represented by $R^1$ includes, for example, a methyl group, an ethyl group, a propyl group, a butyl group or the like, while the acyl group represented by $R^1$ includes a formyl group, an acetyl group, a propionyl group, benzoyl group or a benzyloxycarbonyl group. Further, where $R^2$ is a lower alkyl group, it is, for example, a methyl group, an ethyl group or the like.

In order to carry out the present invention, a racemic compound of a p-hydroxyphenylglycine derivative is reacted with optically active α-phenylethylamine in equivalent amount to yield a phenylethylamine salt of the p-hydroxyphenylglycine derivative. This reaction is preferably carried out in solvent. Said reaction is preferably carried out at a temperature of 50° – 100° C for 0.5 – 3 hours. The solvent is preferably a polar solvent, particularly water, a lower alcohol such as methanol, ethanol, propanol or the like, or a mixture thereof. In this instance, if the p-hydroxyphenylglycine derivative which is used in such that, in the aforementioned formula $R^1$ is a hydrogen atom and $R^2$ is a phenyl group or a benzyloxy group, the lower alcohol is preferred as solvent. On the other hand, if $R^1$ is a lower alkyl group or an acyl group and $R^2$ is a hydrogen atom, a lower alkyl group, a phenyl group or a benzyloxy group, either water or the lower alcohol may be employed suitably.

In the production of a phenylethylamine salt of the optically active p-hydroxyphenylglycine derivative, a D-antipode can be obtained in the form of crystals of an optically active diastereomer salt with high purity when the p-hydroxyphenylglycine derivative is such that in the aforementioned general formula $R^1$ is a hydrogen atom or an acyl group and $R^2$ is a hydrogen atom, a lower alkyl group, a phenyl group or a benzyloxy group, and is reacted with d—(+) α-phenylethylamine. Furthermore, where the p-hydroxyphenylglycine derivative which is used in such that $R^1$ is a lower alkyl group and $R^2$ is a hydrogen atom, the lower alkyl group, a phenyl group or a benzyloxy group and is reacted with l—(—) α-phenylethylamine, a diastereomer of D-antipode can also be formed.

In the mother liquor which allows the diastereomer salt to crystallize, there exists the other diastereomer salt in large amount, so that the other diastereomer can be obtained by subjecting the mother liquor to concentration under reduced pressure, separating the resultant crystals by filtration and recrystallizing the thus separated crystals with a suitable solvent several times.

From the above it will be clear that diastereomer salts with a desired D- or L-antipode can be readily obtained by suitably choosing, in combination, the proper substituent group of $R^1$ and the proper type of optically active α-phenylethylamine to be used.

It should be noted that the above-mentioned two kinds of diastereomer salts, i.e., the α-phenylethylamine salts of p-hydroxyphenylglycine derivatives are novel compounds, respectively.

The conversion of the diastereomer salts to optically active p-hydroxyphenylglycine derivatives is feasible by treating the salts with an acid such as hydrochloric acid or an alkali such as sodium hydroxide, potassium hydroxide or sodium carbonate. Where an acid is used as a treating agent, the p-hydroxyphenylglycine derivatives are yielded in the form of crystals, which may be separated by filtration, while where an alkali is used, α-phenylethylamine which is separated in a free state is first removed by extraction by the use of an organic solvent such as ether, chloroform, benzene or the like and then the resultant residual solution is made acidic by means of an acid to obtain crystals of optically active p-hydroxyphenylglycine derivatives, followed by seperation of the crystals from the solution by filtration.

The resultant optically active p-hydroxyphenylglycine derivatives are then hydrolyzed by means of hydrochloric acid, sulfuric acid, hydrobromic acid, or hydroiodic acid, followed by neutralization with an alkali to obtain p-hydroxyphenylglycine with a desired optical activity. The hydrolysis reaction can be generally carried out at a temperature ranging from room temperatuure to 200° C for 0.5 to 24 hours, preferably at the boiling point of the aqueous solution of acid for about 1 to 5 hours.

The optically active α-phenylethylamine employed in the reaction may be recovered by the following manner. That is, where an acid is employed as the diastereomer salt-treating agent, the α-phenylethylamine is dissolved in the form of an acid salt in the mother liquor obtained after filtering off the optically active p-hydroxyphenylglycine derivative crystals, so that the same can be recovered at a high yield by making the filtrate alkaline by means of an alkali, subjecting the resultant filtrate to extraction with an organic solvent, and fractionating the resultant extract to obtain the α-phenylethylamine.

On the other hand, where an alkali is used as the treating agent, the treated solution may be directly subjected to extraction using an organic solvent, followed by treating the extract in a manner as mentioned above to recover the α-phenylethylamine. The thus recovered α-phenylethylamine may be reused as a reaction agent in a fresh reaction system.

As will be apparent from the foregoing, the process of the present invention is extremely advantageous in that optically active p-hydroxyphenylglycine with high purity can be prepared on an industrial scale by using optically active α-phenylethylamine, which is easily available, as a resolving agent.

Among optically active p-hydroxyphenylglycine isomers obtained by the process of the present invention, the D-antipode is very useful as a starting material for semi-synthetic penicillin or semi-synthetic cephalosporin.

The invention will be particularly illustrated by the following examples.

EXAMPLE 1

10.0 g of DL-N, O-diacetyl-p-hydroxyphenylglycine, 5.28 g of d—(+)-α-phenylethylamine, and 100 ml of water were mixed with each other and the mixture was heated up to about 80° C until the contents were completely dissolved in water. Then, the resultant solution was allowed to stand at 40° C for 1 hour to crystallize d—(+)-α-phenylethylamine-D-N, O-diacetyl-p-hydroxyphenylglycinate, m.p. 186° – 188° C, $[\alpha]_D^{25} = -98.0°$ ($c=1$, MeOH). The resultant crystals were separated by filtration and then dissolved in 60 ml of water while heating, followed by allowing the resultant solution to stand at 40° C for 1 hour to obtain 4.2 g of purified crystals of D-antipode, m.p. 190.5° – 191.5° C, $[\alpha]_D^{24} = -102.4°$ ($c=0.3$, MeOH).

Elementary analysis:

| | Calculated (for $C_{20}H_{24}N_2O_5$) | Found |
|---|---|---|
| C% | 64.33 | 64.53 |
| H% | 6.47 | 6.48 |
| N% | 7.50 | 7.74 |

10% aqueous sodium carbonate solution was added to 4.2 g of the crystal to adjust to about pH 9. The free d—(+)-α-phenylethylamine was extracted with ether, while the pH of the water layer was adjusted to 1 – 2 by means of hydrochloric acid to obtain 1.5 g of D-N, O-diacetyl-p-hydroxyphenylglycine, m.p. 213° C, $[\alpha]_D^{20} = -213.3°$ ($c=1$, MeOH), which was then hydrolyzed with 2N-hydrochloric acid for 2 hours under reflux, followed by the treatment with a 10% aqueous sodium carbonate solution for making the pH of the resultant solution at 6 – 7 thereby to obtain 0.9 g of D-p-hydroxyphenylglycine, m.p. 240 – 242° C(dec.), $[\alpha]_D^{24} = -160.0°$ ($c=1$, N-HCl).

EXAMPLE 2

1.0 g of DL-N-acetyl-p-methoxyphenylglycine and 0.54 g of l—(—)-α-phenylethylamine were mixed with 20 ml of ethanol and were dissolved under reflux. The resultant solution was allowed to stand in an ice house overnight to give 0.48 g of l—(—)-α-phenylethylamine-D-N-acetyl-p-methoxyphenylglycinate in the form of crystals, m.p. 195° – 197° C, $[\alpha]_D^{20} = -108.2°$ ($c=1$, EtOH).

Elementary analysis:

| | Calculated (for $C_{19}H_{24}N_2O_4$) | Found |
|---|---|---|
| C% | 66.26 | 66.01 |
| H% | 7.02 | 7.04 |
| N% | 8.13 | 8.12 |

The crystals were dissolved in 15 ml of water, the pH of which was adjusted to about 2 with concentrated hydrochloric acid, followed by cooling to crystallize D-N-acetyl-p-methoxyphenylglycine. The crystal was separated from the solution by filtration and was mixed with 5 mols of 48% hydrobromic acid under reflux for 3 hours thereby to obtain 0.17 g of D-p-hydroxyphenylglycine, m.p. 240° – 242° C. (dec.).

EXAMPLE 3

4.0 g of DL-N-benzoyl-p-hydroxyphenylglycine and 1.79 g of d—(+)-α-phenylethylamine were mixed with 30 ml of ethanol and dissolved under reflux. The resultant solution was allowed to stand in an ice house overnight to obtain 1.53 g of crystals of d-(+)-α-phenylethylamine-D-N-benzoyl-p-hydroxyphenylglycinate $[\alpha]_D^{32} = -55.1°$ ($c=1$, MeOH), followed by recrystallization to obtain 1.08 g of the purified product, m.p. 189° – 191° C, $[\alpha]_D = -59.0°$ ($c=1$, MeOH).

Elementary analysis:

| | Calculated (for $C_{23}H_{24}N_2O_4$) | Found |
|---|---|---|
| C% | 70.39 | 70.50 |
| H% | 6.16 | 6.29 |
| N% | 7.13 | 7.34 |

To 0.36 g of the crystal was added 0.5 ml of 5N hydrochloric acid, followed by extraction of D-N-benzoyl-p-hydroxyphenylglycine with ether. Then, the ether was removed by distillation to obtain 0.21 g of the purified glycine compound, m.p. 159° – 161° C $[\alpha]_D^{32} = -163.2$ ($c=1$, MeOH). The thus obtained glycine compound was treated in the same manner as in Example 1 to obtain 0.11 g of p-hydroxyphenylglycine, m.p. 240° – 242° C (dec.).

EXAMPLE 4

4.0 g of DL-N-benzyloxycarbonyl-p-hydroxyphenylglycine and 1.61 g of d—(+)-α-phenylethylamine were mixed with 25 ml of ethanol and dissolved under reflux, followed by allowing the resultant solution to stand in an ice house overnight to obtain 1.55 g of d—(+)-α-phenylethylamine-D-N-benzyloxycarbonyl-p-hydroxyphenylglycinate. The thus obtained glycinate was recrystallized two times with ethanol to obtain 0.68 g of a purified product, m.p. 190.5° – 191.0191.0 C. $[\alpha]_D^{30}$ = −59.8° ($c$=1, MeOH). Elementary analysis:

|  | Calculated (for $C_{24}H_{26}N_2O_5$) | Found |
|---|---|---|
| C% | 63.78 | 62.58 |
| H% | 5.02 | 5.16 |
| N% | 4.65 | 4.57 |

0.6 g of the crystal was added with 0.5 ml of 5N hydrochloric acid to make acid, followed by extracting D-N-benzyloxycarbonyl-p-hydroxyphenylglycine with ether. Then, the ether was removed by distillation to obtain 0.43 g of a purified product, m.p. 159° – 161° C, $[\alpha]_D^{26}$ = −116.0° ($c$=1, MeOH).

Thereafter, the purified product was treated in the same manner as in Example 1 to obtain 0.21 g of D-p-hydroxyphenylglycine, m.p. 240° – ° C (dec.).

What is claimed is:

1. A process for the preparation of optically active p-hydroxyphenylglycine, which comprises reacting a racemic compound of a p-hydroxyphenylglycine derivative represented by the following general formula

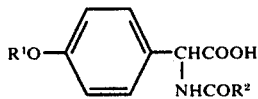

(wherein $R^1$ represents a hydrogen atom, a lower alkyl group or an acyl group and $R^2$ represents a hydrogen atom, a lower alkyl group, a phenyl group or a benzyloxy group) with optically active α-phenylethylamine in a solvent to form a corresponding salt, subjecting said salt to fractional crystallization for optical resolution to obtain two kinds of optically active salts, decomposing at least one of said two kinds of optically active salts by means of an acid or an alkali to obtain the respective optically active p-hydroxyphenylglycine derivative, and hydrolyzing said derivative with an acid selected from the group consisting of hydrochloric acid, sulfuric acid, hydrobromic acid and hydroidic acid.

2. A process according to claim 1, wherein $R^1$ is a member selected from the group consisting of a hydrogen atom, a methyl group and an acetyl group, and $R^2$ is a member selected from the group consisting of a methyl group, a phenyl group and a benzyloxy group.

3. A process according to claim 1, wherein $R^1$ is an acetyl grouup and $R^2$ is a methyl group.

4. A process according to claim 1, wherein said solvent is a member selected from the group consisting of water, methanol, ethanol, propanol and a mixture thereof.

5. A process according to claim 1, wherein said racemic compound of a p-hydroxyphenylglycine derivative is reacted with said optically active α-phenylethylamine at a temperature of 50° – 100° C for 0.5 – 3 hours.

6. A process according to claim 1, wherein said hydrolysis is carried out at a temperature of about 25° – 200° C for about 0.5 – 24 hours.

7. d—(+)-α-phenylethylamine-D-N,O-diacethyl-p-hydroxyphenylglycinate.

8. l—(−)-α-phenylethylamine-D-N-acetyl-p-methoxyphenylglycinate.

9. d—(+)-α-phenylethylamine-D-N-benzoyl-p-hydroxyphenylglycinate.

10. d—(+)-α-phenylethylamine-D-N-benzyloxycarbonyl-p-hydroxyphenylglycinate.

* * * * *